(12) United States Patent
Waldrop, III et al.

(10) Patent No.: US 8,308,352 B1
(45) Date of Patent: Nov. 13, 2012

(54) THERMAL SHOCK APPARATUS FOR SIMULATING ONE-SIDED OPERATIONAL THERMAL GRADIENTS

(75) Inventors: John C. Waldrop, III, Saint Charles, MO (US); Daniel J. Perron, Federal Way, WA (US); Laura Sullivan Riegel, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 816 days.

(21) Appl. No.: 12/464,343

(22) Filed: May 12, 2009

(51) Int. Cl.
*G01N 3/60* (2006.01)
*G01K 17/00* (2006.01)
(52) U.S. Cl. ............... 374/57; 374/5; 374/12; 73/865.6
(58) Field of Classification Search ............... 374/45, 374/57, 4, 5, 12, 13, 208; 73/864.51, 864.59, 73/864.63, 864.91, 865.6; 432/32, 225
See application file for complete search history.

(56) References Cited

U.S. PATENT DOCUMENTS

| | | | |
|---|---|---|---|
| 3,381,897 A | 5/1968 | Wennerstrom | |
| 3,422,678 A * | 1/1969 | Murray | 374/126 |
| 3,553,002 A | 1/1971 | Haraway, Jr. et al. | |
| 3,664,181 A * | 5/1972 | Conrad et al. | 73/571 |
| 4,575,257 A * | 3/1986 | Ogura et al. | 374/45 |
| 5,193,910 A * | 3/1993 | Kinoshita | 374/45 |
| 5,560,569 A | 10/1996 | Schmidt | |
| 5,613,776 A * | 3/1997 | Turner et al. | 374/57 |
| 5,907,246 A * | 5/1999 | Abraham et al. | 324/750.08 |
| 5,974,902 A * | 11/1999 | Scofield | 73/865.6 |
| 6,123,452 A * | 9/2000 | Uchimura et al. | 374/57 |
| 6,227,701 B1 * | 5/2001 | Wu | 374/57 |
| 6,886,976 B2 * | 5/2005 | Gaasch et al. | 374/5 |
| 7,540,656 B1 * | 6/2009 | Stochl et al. | 374/29 |
| 2007/0071063 A1 * | 3/2007 | Liu et al. | 374/15 |
| 2008/0053200 A1 * | 3/2008 | Dhellemmes et al. | 73/49.8 |

FOREIGN PATENT DOCUMENTS

JP 2006084376 A * 3/2006

* cited by examiner

*Primary Examiner* — R. A. Smith
(74) *Attorney, Agent, or Firm* — Klintworth & Rozenblat IP LLC (57) ABSTRACT

An apparatus for single-side, thermal shock testing of a specimen may comprise a base and thermal insulation. The base may comprise an internal cavity disposed within the base. The internal cavity may extend through a first outer surface of the base. A specimen-supporting surface may be recessed within the first outer surface for supporting a specimen within the base to substantially close the internal cavity. The thermal insulation may not substantially cover the first outer surface, but may substantially cover other outer surfaces of the base.

27 Claims, 7 Drawing Sheets

FIG. 7

THERMAL SHOCK APPARATUS FOR SIMULATING ONE-SIDED OPERATIONAL THERMAL GRADIENTS

FIELD OF THE INVENTION

The disclosure relates to apparatus and methods for single-side, thermal shock testing of a specimen.

BACKGROUND OF THE DISCLOSURE

Some devices and/or materials in operation may experience extreme low or high temperatures on one side, such as on an exterior of the device, but no significant temperature extreme on another side, such as an inside of the device. Some of these representative devices and/or materials may include: thruster nozzles of satellites and launch vehicles, cryogenic tanks; radomes; apertures; hypersonic inlets; high speed control surfaces; rocket nozzles; ablators; space mirrors; pyrotechnic gas generators; thermal batteries; high-temperature EMI shields and gaskets; specialty coatings; rigid insulators; aerogels; CMC ceramics; monolithic ceramics; and/or other types of devices and materials. As a result of the single-side, thermal shock experienced by these devices and/or materials, a large thermal gradient may be experienced through a thickness of the devices or materials. This large thermal gradient may alter the performance of the devices or materials, and/or may lead to failure.

Some existing apparatus and/or methods for testing a specimen, in order to determine the single-side, thermal shock experienced by such devices or materials, may include: Quartz infrared banks; laser irradiation; high speed wind tunnels; arc jet test chambers; and hot plates. However, these apparatus and/or methods, with the exception of the hot plate, may require elaborate setups, equipment, and controls that may be extremely costly. The hot plate may have limitations including: potential altering of the tested specimen's performance due to physical contact of the heater with the specimen; low heating rate potential, and temperature variations, during the testing, across the heated surface of the specimen.

An apparatus and/or method is needed which may solve one or more problems of one or more of the conventional apparatus and methods for single-side, thermal shock testing of a specimen.

SUMMARY OF THE DISCLOSURE

In one embodiment, an apparatus for single-side, thermal shock testing of a specimen is disclosed. The apparatus may comprise a base and thermal insulation. The base may comprise an internal cavity disposed within the base. The internal cavity may extend through a first outer surface of the base. A specimen-supporting surface may be recessed within the first outer surface for supporting a specimen within the base to substantially close the internal cavity. The thermal insulation may not substantially cover the first outer surface, but may substantially cover other outer surfaces of the base.

In another embodiment, an apparatus for single-side, thermal shock testing of a specimen is disclosed. The apparatus may comprise a base, at least one securing device, a retention cage, and thermal insulation. The base may comprise first and second opposed outer surfaces. An internal cavity may be disposed between the first and second opposed outer surfaces. The internal cavity may extend through the first outer surface. At least one perimeter outer surface may extend between the first and second opposed outer surfaces around the internal cavity. A specimen-supporting surface may be recessed within the first outer surface. The specimen-supporting surface may support the specimen in order to substantially close the internal cavity. The at least one securing device may secure the specimen against the specimen-supporting surface. The base may be disposed within the retention cage. The thermal insulation may be disposed between the retention cage and the base. The thermal insulation may substantially cover the at least one perimeter outer surface and the second opposed outer surface, but may not substantially cover the first opposed outer surface and the specimen.

In yet another embodiment, a method of single-side, thermal shock testing of a specimen is disclosed. In one step, an apparatus may be provided. The apparatus may comprise a base, and thermal insulation. An internal cavity may be disposed within the base. The internal cavity may extend through a first outer surface of the base. A specimen-supporting surface may be recessed within the first outer surface. The thermal insulation may not substantially cover the first outer surface but may substantially cover other outer surfaces of the base. In another step, the specimen may be disposed on the specimen-supporting surface to substantially close the internal cavity of the base. In an additional step, the specimen may be secured against the specimen-supporting surface using at least one securing device. In still another step, an exposed surface of the specimen, which is not thermally insulated, may be at least one of heated and cooled, while other surfaces of the specimen may be thermally insulated.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
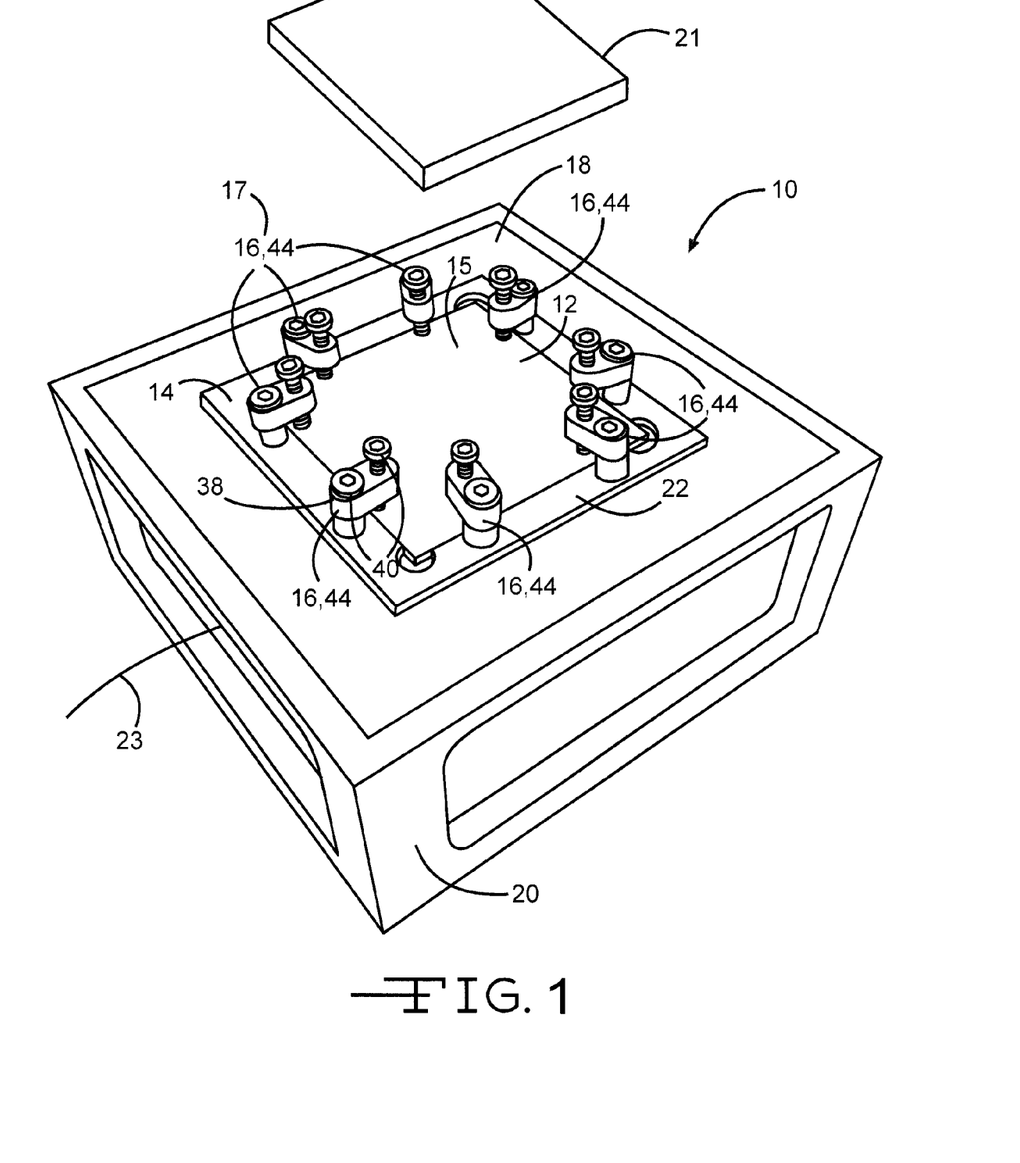
FIG. 1 illustrates a top perspective view of one embodiment of an apparatus for single-side, thermal shock testing of a specimen.

FIG. 1 illustrates a top perspective view of one embodiment of an apparatus 10 for single-side, thermal shock testing of a specimen 12. The specimen 12 being tested may comprise a portion or material of one or more of the following devices or materials: a thruster nozzle of a satellite; a cryogenic tank; a radome; a hypersonic inlet; a rocket nozzle; an ablator; a space mirror; a high-temperature EMI shield and gasket; a specialty coating; a rigid insulator; an aerogel; a CMC ceramic; a monolithic ceramic; and/or other types of devices or materials which require evaluation in order to determine when they may fail under extreme environmental conditions.

Figure 2:
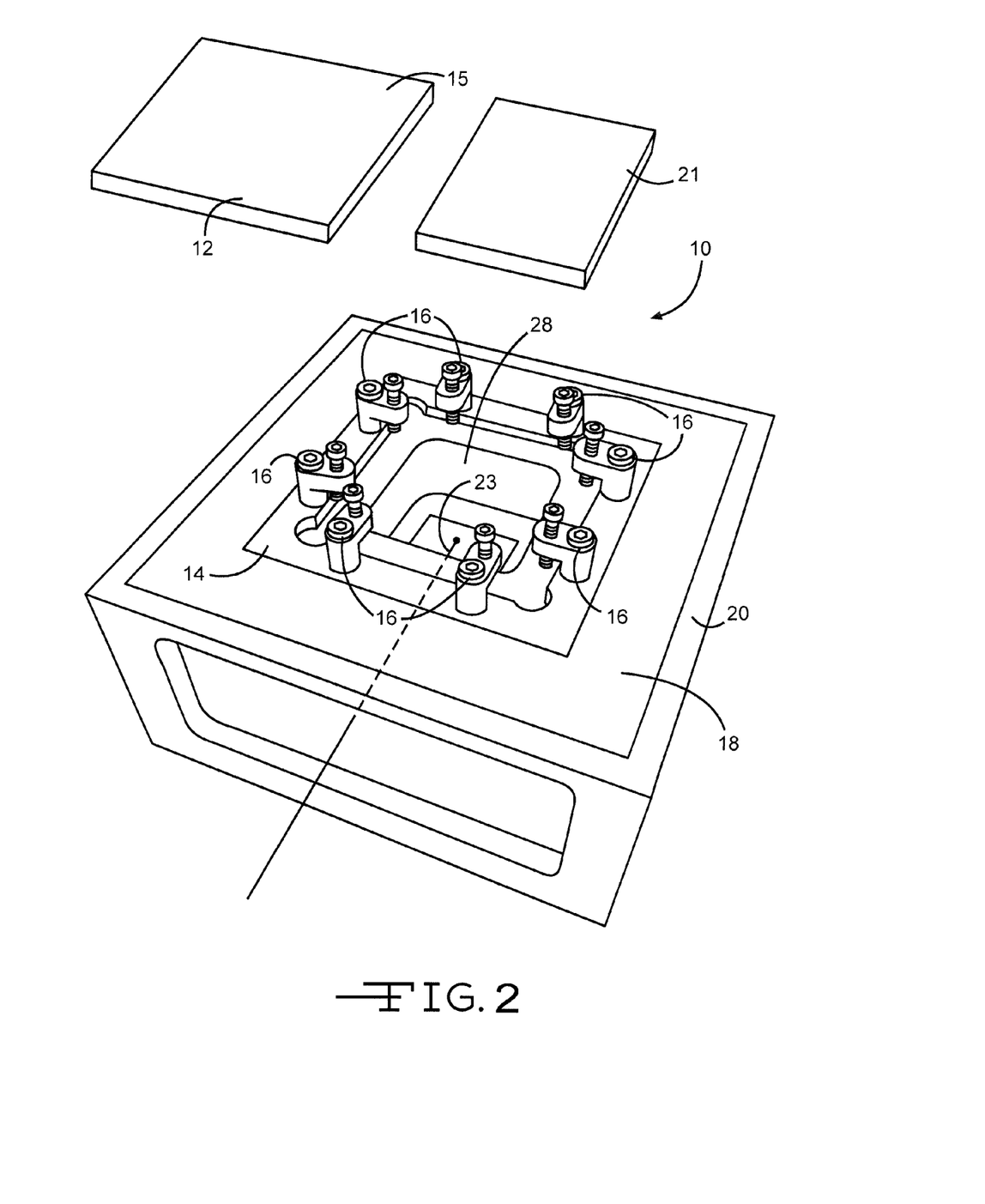
FIG. 2 illustrates a top perspective view of the apparatus of FIG. 1 with the specimen removed from the apparatus.
Figure 3:
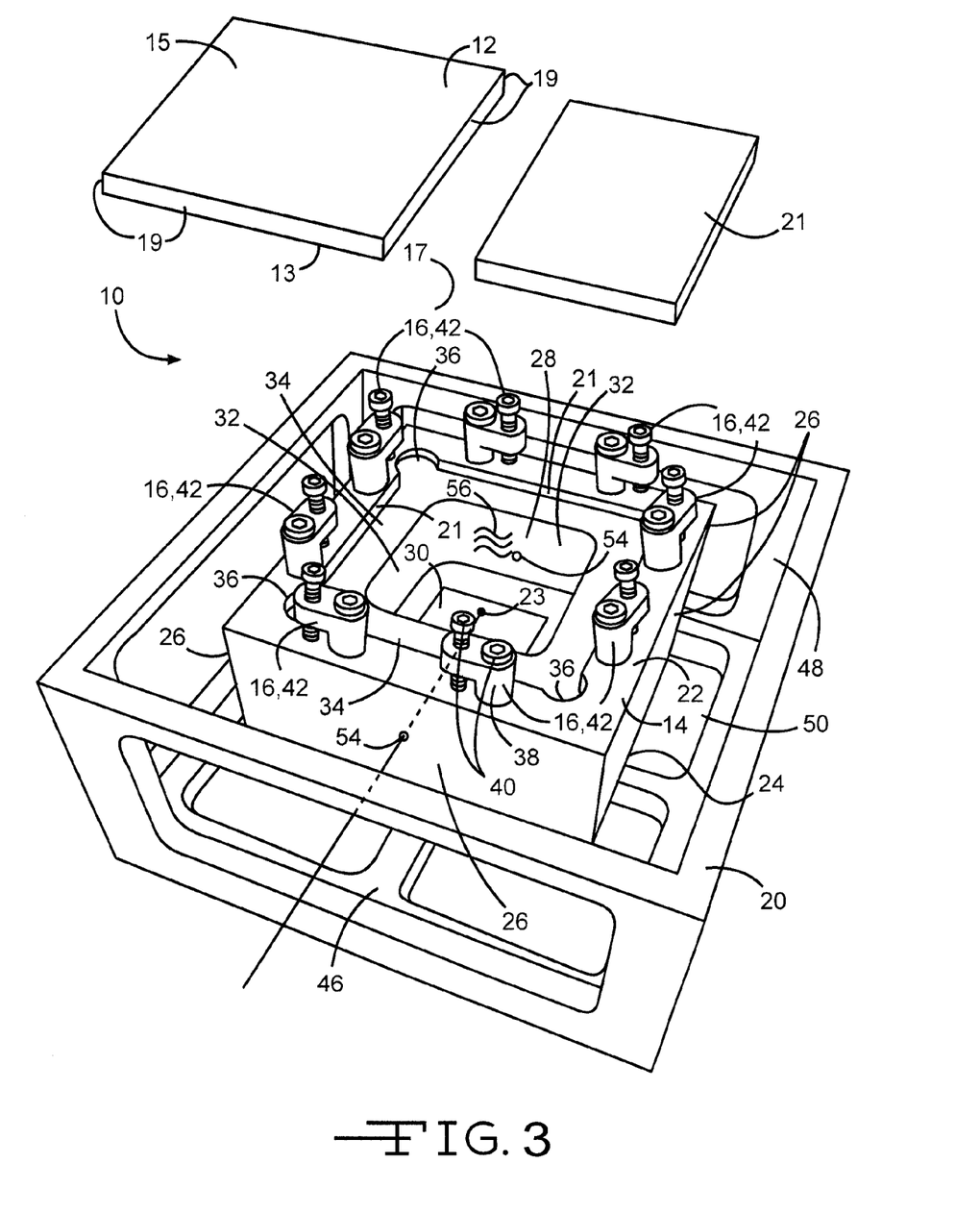
FIG. 3 illustrates a top perspective view of the apparatus of FIG. 2 with thermal insulation removed from the apparatus.

As shown in FIG. 1, the apparatus 10 may comprise a base 14, at least one securing device 16, thermal insulation 18, a retention cage 20, a temperature-changing device 21, and/or a thermocouple 23. FIG. 2 illustrates a top perspective view of the apparatus 10 of FIG. 1 with the specimen 12 removed from the base 14. FIG. 3 illustrates a top perspective view of the apparatus 10 of FIG. 2 with the thermal insulation 18 removed.

As shown in FIG. 3, the base 14 may be rectangular. In other embodiments, the shape of the base 14 may vary. The base 14 may comprise opposing first and second outer surfaces 22 and 24, and at least one perimeter outer surface 26. The opposed first and second outer surfaces 22 and 24 may respectively comprise top and bottom outer surfaces of the base 14. The at least one perimeter outer surface 26 may extend between the opposed first and second outer surfaces 22 and 24 around an internal cavity 28 disposed within the base 14. The at least one perimeter outer surface 26 may comprise outer side surfaces of the base 14. The internal cavity 28 may extend between the opposed first and second outer surfaces 22 and 24, and may extend through the first outer surface 22. The internal cavity 28 may comprise a bottom internal cavity surface 30, and at least one perimeter internal cavity side surface 32 extending around the internal cavity 28. The internal cavity 28 may be substantially closed within the base 14 with the exception of extending through the first outer surface 22 of the base 14.

A specimen-supporting surface 34 may be recessed within the first outer surface 22 around the internal cavity 28. The specimen-supporting surface 34 may be substantially parallel to the first outer surface 22. The specimen-supporting surface 34 may be used to support the specimen 12 to substantially close the internal cavity 28 as shown in FIG. 1. When, as shown in FIG. 1, the specimen 12 is supported on the specimen-supporting surface 34, a bottom surface 13 (shown in FIG. 3) of the specimen 12 may substantially cover the internal cavity 28, while a top opposed surface 15 (shown in FIG. 3) of the specimen 12 may be exposed to an atmosphere 17 outside of the internal cavity 28. When in the position shown in FIG. 1, the top opposed surface 15 of the specimen 12 may be substantially flush with the first outer surface 22 of the base 14. Also, when in the position shown in FIG. 1, side surfaces 19 (shown in FIG. 3) of the specimen 12 may be disposed against recessed side-surfaces 21 (shown in FIG. 3) extending substantially perpendicularly between the first outer surface 22 and the recessed specimen-supporting surface 34.

As shown in FIG. 3, the first outer surface 22 may comprise at least one grip opening 36 disposed in the first outer surface 22 adjacent to the recessed specimen-supporting surface 34. The at least one grip opening 36 may be used to grip the specimen 12 supported by the recessed specimen-supporting surface 34. The base 14 may be made of steel, or a super-alloy such as Haynes 230, or Inconel 625 for improved temperature resistance. Another type of material, such as Monolithic Alumina Ceramic, may be used for the base 14 for even high temperature testing.

The at least one securing device 16 may be used to secure and un-secure the specimen 12 from the specimen-supporting surface 34. The at least one securing device 16 may comprise at least one rotate-able collar 38 and at least one screw 40. The at least one securing device 16 may be adapted to rotate between an open position 42 disposed away from the recessed specimen-supporting surface 34 and the specimen 12, as shown in FIG. 3, and a closed position 44 disposed over the recessed specimen-supporting surface 34 (shown in FIG. 3) and against the specimen 12, as shown in FIG. 1. In the open position 42 of FIG. 3, the specimen 12 may be unsecured so that it may be moved against and removed from the recessed specimen-supporting surface 34. In the closed position 44 of FIG. 1, the specimen 12 may be secured with the at least one screw 40 against the recessed specimen-supporting surface 34 (shown in FIG. 3). The at least one securing device 16 may be made of steel, or a super-alloy such as Haynes 230, Inconel 625, or another type of material.

As shown in FIG. 3, the base 14 may be disposed within the retention cage 20. The retention cage 20 may comprise a bottom surface 46 supporting the base 14, at least one side surface 48 disposed around the at least one perimeter outer surface 26 of the base 14, and an open top end 50 adjacent to the first outer surface 22 of the base 14. The retention cage 20 may be made of steel, or a super-alloy such as Haynes 230, Inconel 625, or another type of material.

As shown in FIGS. 1 and 2, the thermal insulation 18 may be disposed between the retention cage 20 and the base 14. The thermal insulation 18 may comprise an Alumina blanket, Saffil, Min-K, or another type of material. The thermal insulation 18 may substantially cover the at least one perimeter outer surface 26 (shown in FIG. 3) of the base 14 and the second opposed outer surface 24 (shown in FIG. 3) of the base 14. The thermal insulation 18 may not substantially cover the first opposed surface 22 of the base 14 or the specimen 12. In such manner, the thermal insulation 18 may substantially insulate all outer surfaces 24 and 26 of the base with the exception of the first outer surface 22.

As shown in FIG. 1, when the specimen 12 is disposed within the base 14 against the recessed specimen-supporting surface 34 (shown in FIG. 3), the bottom surface 13 (shown in FIG. 3) and side surfaces 19 (shown in FIG. 3) of the specimen 12 may be thermally insulated. This may be as a result of surfaces 13 and 19 (shown in FIG. 3) of the specimen 12 being recessed within the base 14 which has its second outer surface 24 (shown in FIG. 3) and the at least one perimeter outer surface 26 (shown in FIG. 3) insulated with the thermal insulation 18. However, when the specimen 12 is in this position, the top surface 15 (shown in FIG. 3) of the specimen 12 may not be thermally insulated due to the thermal insulation 18 not substantially covering the top surface 15 of the specimen 12 or the first outer surface 22 of the base 14. As a result, this configuration may allow for single-sided, thermal shock testing of the top surface 15 of the specimen 12 while the other surfaces 13 and 19 (shown in FIG. 3) of the specimen 12 are thermally insulated.

As shown in FIG. 1, the apparatus 10 and the specimen 12 may be disposed adjacent to the temperature-changing device 21. The temperature-changing device 21 may comprise at least one of a chamber, an oven, a furnace, a heating device, and a cooling device. The temperature-changing device 21 may be used to at least one of heat and cool the atmosphere 17 adjacent to the specimen 12 in order to heat or cool the specimen 12. The temperature-changing device 21 may directly heat or cool an exposed, un-insulated, top surface 15 of the specimen 12.

As shown in FIG. 3, at least one cavity opening 54 may extend through the at least one perimeter outer surface 26 through the at least one perimeter internal cavity side surface 32 into the internal cavity 28. In other embodiments, the at least one cavity opening 54 may extend through the second outer surface 24 through the bottom internal cavity surface 30 into the internal cavity 28. The at least one cavity opening 54 may be used to vent gases 56 out of the internal cavity 28, to feed gases 56 into the internal cavity 28, and/or to insert the thermocouple 23 into the internal cavity 28 to take a temperature reading.

Figure 4:
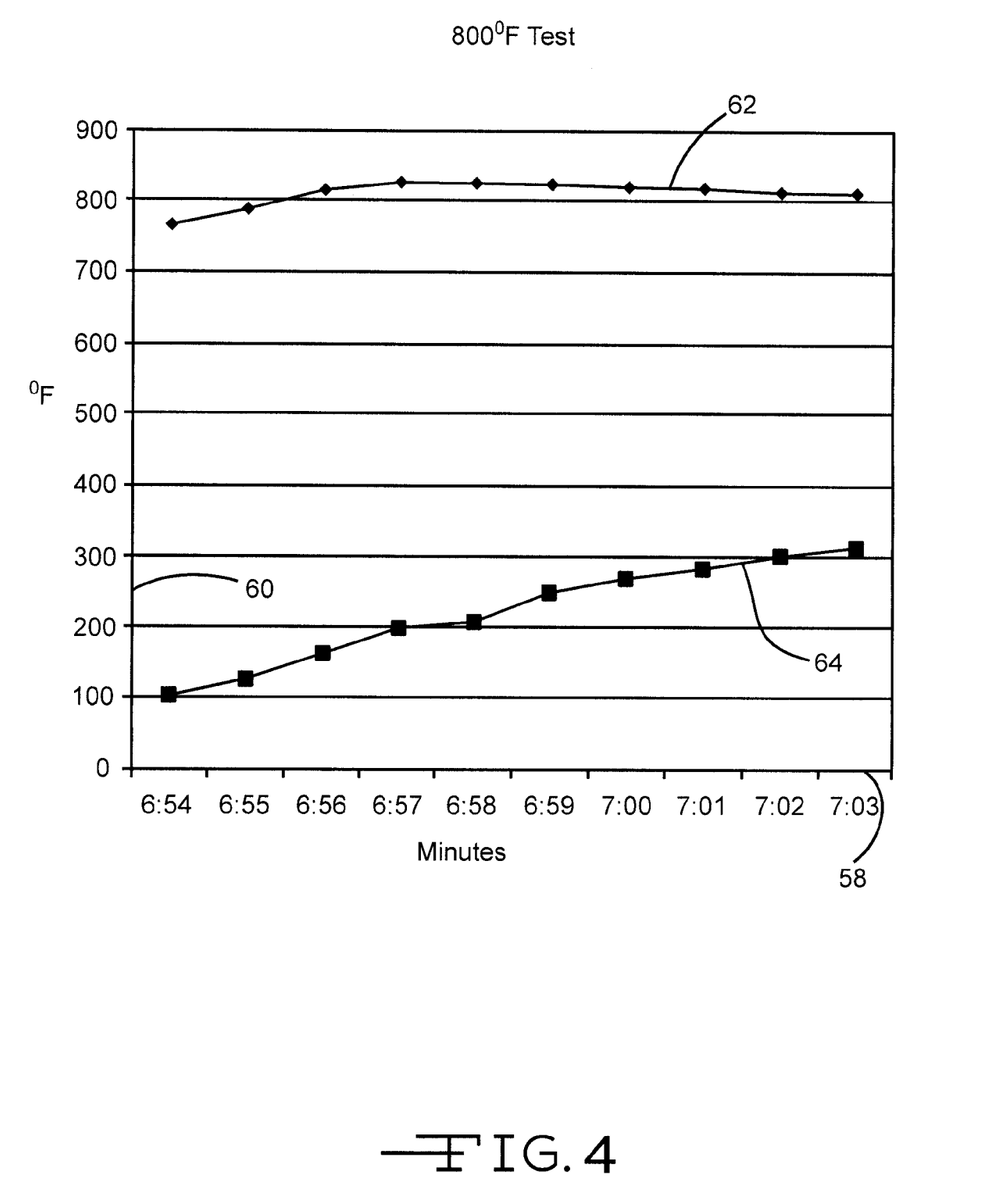
FIG. 4 illustrates a chart showing test results from testing a specimen, using one embodiment of an apparatus, at an approximate temperature of 800 degrees Fahrenheit.

FIG. 4 is a chart showing test results from testing the specimen 12, using the apparatus 10, at approximately a temperature of 800 degrees Fahrenheit. The X-axis 58 shows exposure time in minutes, from a time-period between 6:54 minutes to 7:03 minutes, and the Y-Axis 60 shows temperature in degrees Fahrenheit over that time-period. The temperature-changing device temperature 62 was maintained, for approximately 7 minutes, at approximately 800 degrees Fahrenheit, while the temperature 64 of the internal cavity 28 of the apparatus 10 varied between approximately 100 degrees Fahrenheit and 300 degrees Fahrenheit. During this time, due to the use of the apparatus 10, the top surface 15 of the specimen 12 was exposed, without insulation, to the thermal shock of 800 degrees Fahrenheit, while the bottom surface 13 and side surfaces 19 of the specimen 12 were substantially insulated as evidenced by the temperature 64 of the internal cavity 28.

Figure 5:
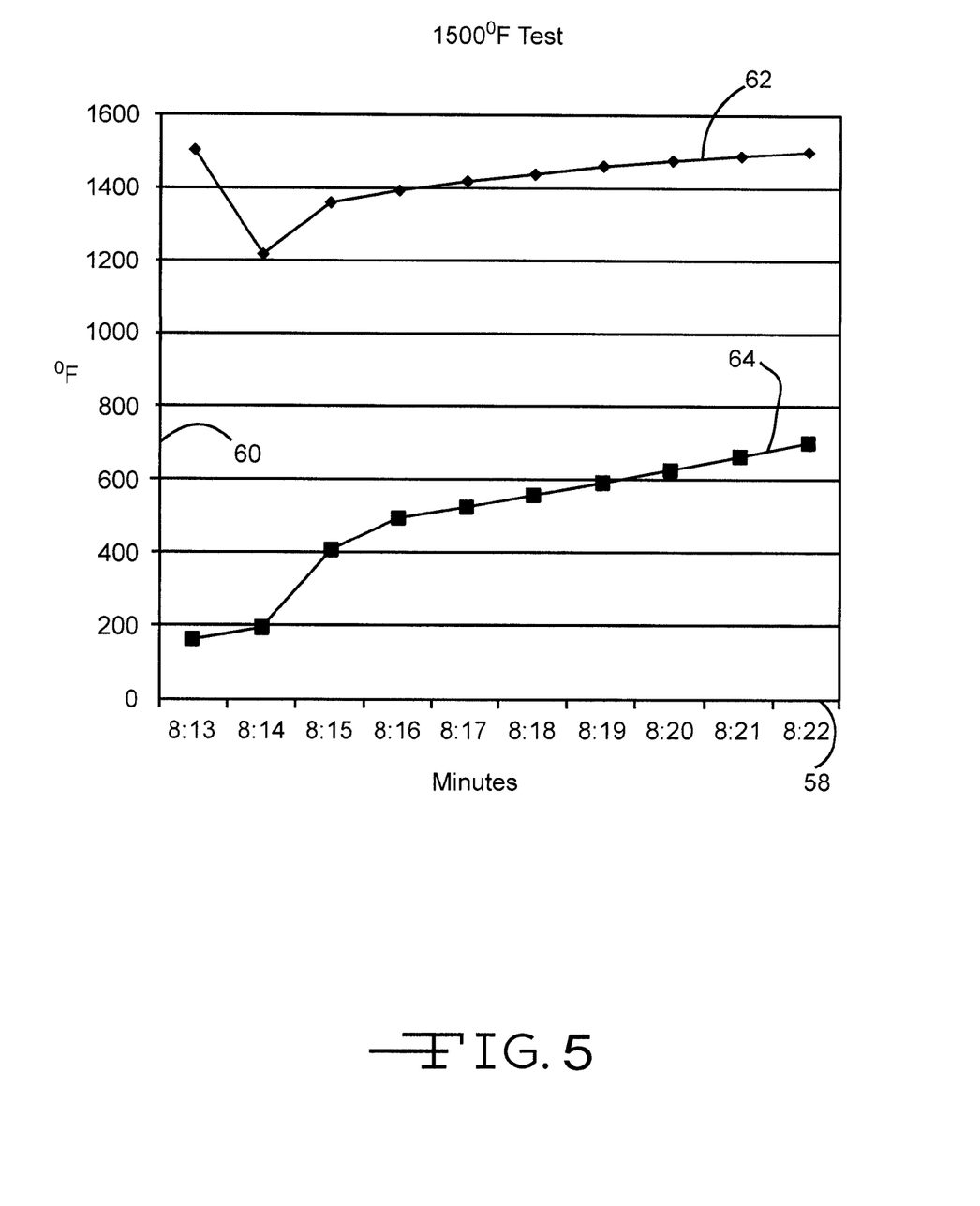
FIG. 5 illustrates a chart showing test results from testing a specimen, using one embodiment of an apparatus, at an approximate temperature of 1,500 degrees Fahrenheit.

FIG. 5 is a chart showing test results from testing the specimen 12, using the apparatus 10, at approximately a temperature of 1,500 degrees Fahrenheit. The X-axis 58 shows exposure time in minutes, from a time-period between 8:13 minutes to 8:22 minutes, and the Y-Axis 60 shows temperature in degrees Fahrenheit over that time-period. The temperature-changing device temperature 62 was maintained, for approximately 8.5 minutes, at approximately 1,500 degrees Fahrenheit, while the temperature 64 of the internal cavity 28 of the apparatus 10 varied between approximately 200 degrees Fahrenheit and 700 degrees Fahrenheit. During this time, due to the use of the apparatus 10, the top surface 15 of the specimen 12 was exposed, without insulation, to the thermal shock of 1,500 degrees Fahrenheit, while the bottom surface 13 and side surfaces 19 of the specimen 12 were substantially insulated as evidenced by the temperature 64 of the internal cavity 28.

Figure 6:
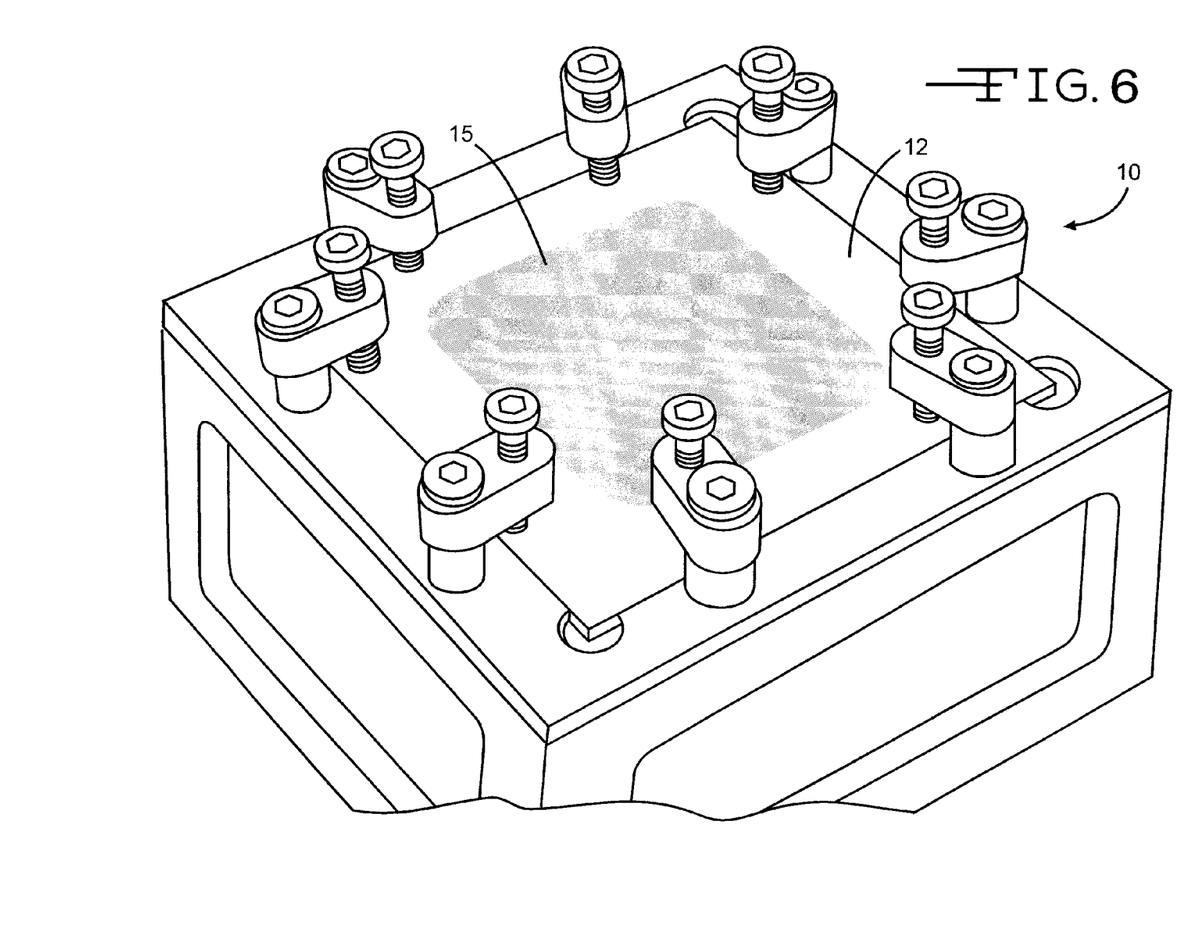
FIG. 6 illustrates a top, partial, close-up view of a top surface of a specimen, disposed within one embodiment of an apparatus, after the specimen was thermal shock tested at a high temperature.

FIG. 6 illustrates a top, partial, close-up view of the top surface 15 of the specimen 12, disposed within the apparatus 10, after the specimen 12 was thermal shock tested at a high temperature. As shown, the top surface 15 of the specimen 12 is discolored from direct, un-insulated exposure to the extreme heat.

Figure 7:
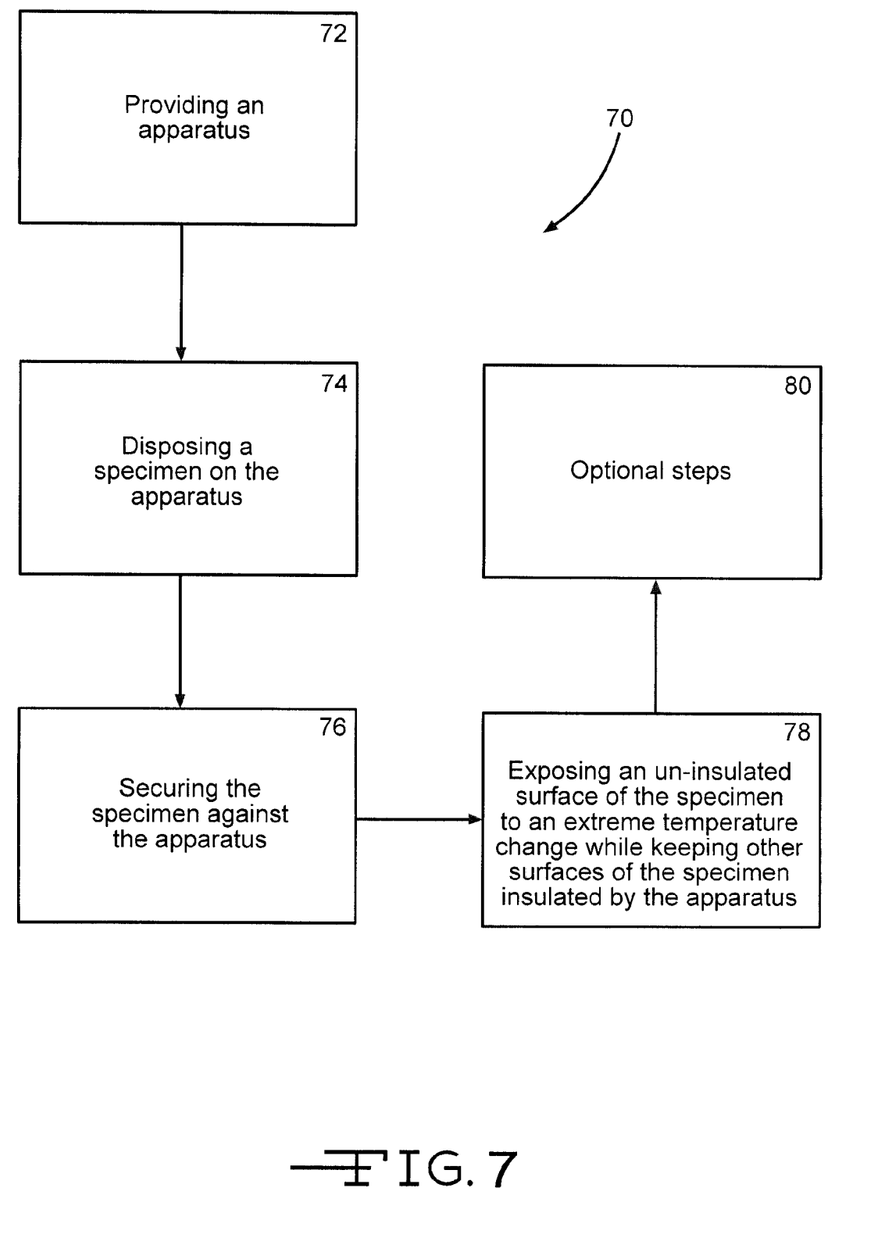
FIG. 7 illustrates a flowchart of one embodiment of a method for single-side, thermal shock testing of a specimen.

FIG. 7 is a flowchart of one embodiment of a method 70 of single-side, thermal shock testing of a specimen 12. In step 72, an apparatus 10 may be provided. The provided apparatus 10 may comprise a base 14 comprising an internal cavity 28 disposed within the base 14. The internal cavity 28 may extend through a first outer surface 22 of the base 14. A specimen-supporting surface 34 may be recessed within the first outer surface 22. Thermal insulation 18 may not substantially cover the first outer surface 22 but may substantially cover other outer surfaces 24 and 26 of the base 14. The base 14 may be disposed within a retention cage 20, and the thermal insulation 18 may be disposed between the retention cage 20 and the base 14 to substantially cover other outer surfaces 24 and 26 of the base 14. The provided apparatus 10 may further comprise a temperature-changing device 21 comprising at least one of a chamber, an oven, a furnace, a heating device, and/or a cooling device.

In step 74, the specimen 12 may be disposed on the specimen-supporting surface 34 to substantially close the internal cavity 28 of the base 14. In step 76, the specimen 12 may be secured against the specimen-supporting surface 34 using at least one securing device 16. The at least one securing device 16 may comprise at least one rotate-able collar 38 and at least one screw 40. To secure the specimen 12 against the specimen-supporting surface 34, the at least one securing device 16 may be rotated from an open position 42 disposed away from the specimen 12 to a closed position 44 disposed against the specimen 12. In step 78, an exposed surface 15 of the specimen 12 may be heated and/or cooled using the temperature-changing device 21. The exposed surface 15 of the specimen 12 may not be thermally insulated, while other surfaces 13 and 19 of the specimen 12 may be thermally insulated.

One or more optional steps 80 of the method 70 may include one or more of the following: heating an atmosphere 17 outside the internal cavity 28 to at least 2,000 degrees Fahrenheit; cooling the atmosphere 17 outside the internal cavity 28 to at least −320 degrees Fahrenheit; measuring temperatures 64, during the at least one of heating and cooling, within the internal cavity 28; measuring temperatures, during the at least one of heating and cooling, of the atmosphere 17 outside the internal cavity 28; determining a thermal performance of the specimen 12 during the at least one of heating and cooling; determining if the specimen 12 failed during the at least one of heating and cooling; and un-securing the specimen 12 from the specimen-supporting surface 34 by rotating the at least one securing device 16 from the closed position 44 to the open position 42.

One or more embodiments of the apparatus 10 and/or method 70 may allow low cost thermal evaluation of materials or devices that are rapidly heated or cooled on a single side. The apparatus 10 may be insulated and may have a substantial heat sink. When the specimen 12 is mounted on the apparatus 10 and placed adjacent to and/or in the temperature-changing device 21, a thermal gradient may be created through a thickness of the specimen 12. The exposed outside surface 15 of the specimen 12 may immediately change temperature due to the temperature-changing device 21. The temperatures of the insulated surfaces 13 and 19 of the specimen 12 may remain substantially lower than the temperature of the exposed outside surface 15, and may only gradually change due to the thermal conduction through the specimen 12. The thermal response of the specimen 12 may accurately model the conditions experienced by devices and/or materials which may be used in single-side, extreme temperature applications.

One or more embodiments of the disclosure may reduce and/or eliminate one or more problems experienced by one or more of the conventional apparatus and/or methods for single-side, thermal shock testing of a specimen. For instance, one or more embodiments of the disclosure may have one or more of the following benefits: allowing for a non-complex testing setup, equipment, and/or controls; reducing cost of the testing; avoiding the altering of the specimen's performance; providing high heating rate potential; providing even temperature distribution across the specimen during testing; providing accurate testing results of the specimen to accurately mimic the effect of a single-side, thermal shock on a device or material; and/or one or more other types of benefits.

It should be understood, of course, that the foregoing relates to exemplary embodiments of the disclosure and that modifications may be made without departing from the spirit and scope of the disclosure as set forth in the following claims.

We claim:

1. An apparatus for single-side, thermal shock testing of a specimen, the apparatus comprising:

a base comprising an internal cavity disposed within the base, the internal cavity extending through a first outer surface of the base, and a specimen-supporting surface recessed within the first outer surface for supporting a specimen within the base to close access to the internal cavity through the first outer surface;
thermal insulation which does not cover the first outer surface but covers other outer surfaces of the base; and
a thermocouple disposed within the internal cavity.

2. The apparatus of claim 1 wherein the specimen-supporting surface is disposed in a fixed position within the base, and is recessed within the first outer surface around the internal cavity.

3. The apparatus of claim 1 wherein the thermal insulation covers a bottom outer surface of the base, and all outer side surfaces of the base, but does not cover the first outer surface comprising a top outer surface of the base.

4. The apparatus of claim 1 wherein at least one perimeter outer surface of the base is disposed around the internal cavity, and a second outer surface of the base is disposed below the internal cavity, wherein the second outer surface opposes the first outer surface of the base.

5. The apparatus of claim 1 wherein at least one cavity opening extends through the base into the internal cavity with the thermocouple disposed through the at least one cavity opening and disposed within the internal cavity.

6. The apparatus of claim 1 further comprising a temperature changing device spaced apart from the base with air disposed between the base and the temperature changing device.

7. The apparatus of claim 6 wherein the temperature changing device is disposed directly over the internal cavity.

8. The apparatus of claim 1 wherein the first outer surface comprises at least one grip opening disposed adjacent to the recessed specimen-supporting surface for gripping a specimen supported by the recessed specimen-supporting surface.

9. The apparatus of claim 1 further comprising at least one securing device for securing and un-securing a specimen against the recessed specimen-supporting surface.

10. The apparatus of claim 9 wherein the at least one securing device comprises at least one rotate-able collar and at least one screw, wherein the at least one rotate-able collar is adapted to rotate from an open position disposed away from the recessed specimen-supporting surface to a closed position disposed over the recessed specimen-supporting surface.

11. The apparatus of claim 1 further comprising a retention cage, wherein the base is disposed within the retention cage and the thermal insulation is disposed between the retention cage and the base.

12. The apparatus of claim 11 wherein the retention cage comprises a bottom surface supporting the base, at least one side surface disposed around a perimeter of the base, and an open top end which ends at an imaginary plane formed by the first outer surface of the base.

13. The apparatus of claim 1 further comprising a specimen, wherein the specimen is disposed within the base against the specimen-supporting surface with a bottom surface of the specimen and sides surfaces of the specimen thermally insulated due to the base and the thermal insulation, and with a top surface of the specimen not thermally insulated due to the thermal insulation not covering the first outer surface of the base.

14. The apparatus of claim 1 further comprising a specimen, wherein the specimen is disposed within the base against the specimen-supporting surface with the specimen completely covering the internal cavity at the first outer surface of the base.

15. An apparatus for single-side, thermal shock testing of a specimen, the apparatus comprising:
a base comprising first and second opposed outer surfaces, an internal cavity disposed between the first and second opposed outer surfaces, the internal cavity extending through the first outer surface, at least one perimeter outer surface extending between the first and second opposed outer surfaces around the internal cavity, and a specimen-supporting surface which is recessed in a fixed position within the first outer surface and configured to support a specimen so that the specimen completely covers and closes access to the internal cavity through the first outer surface; and
the thermal insulation covering the at least one perimeter outer surface and the second opposed outer surface but not covering the first opposed outer surface.

16. The apparatus of claim 15 further comprising a thermocouple disposed within the internal cavity.

17. The apparatus of claim 15 further comprising a temperature changing device spaced apart from the base with air disposed between the base and the temperature changing device.

18. The apparatus of claim 17 wherein the temperature changing device is disposed directly over the internal cavity.

19. The apparatus of claim 15 further comprising a retention cage, wherein the base is disposed within the retention cage, the retention cage comprises a bottom surface supporting the second opposed outer surface of the base, at least one side surface disposed around the at least one perimeter outer surface of the base, and an open top end which ends at an imaginary plane formed by the first outer surface of the base.

20. The apparatus of claim 15 further comprising at least one securing device configured to secure the specimen against the specimen supporting surface.

21. The apparatus of claim 20 wherein the at least one securing device comprises at least one rotate-able collar and at least one screw, wherein the at least one rotate-able collar is adapted to rotate from a closed position disposed against the specimen and holding the specimen in place against the specimen supporting surface to an open position disposed away from the specimen allowing the specimen to be removed from the specimen supporting surface.

22. A method of single-side, thermal shock testing of a specimen comprising:
disposing a specimen on a specimen-supporting surface of an apparatus that includes a base comprising an internal cavity disposed within the base, the internal cavity extending through a first outer surface of the base, the specimen-supporting surface recessed in a fixed position within the first outer surface, and thermal insulation which does not cover the first outer surface but covers other outer surfaces of the base;
securing the specimen against the specimen-supporting surface using at least one securing device to completely cover and close access to the internal cavity of the base through the first outer surface; and
at least one of heating or cooling an exposed surface of the specimen which is not thermally insulated while other surfaces of the specimen are thermally insulated.

23. The method of claim 22 further comprising disposing a thermocouple within the internal cavity and measuring a temperature within the internal cavity.

24. The method of claim 22 further comprising disposing a temperature changing device such that the temperature changing device is spaced apart from the base with air disposed between the base and the temperature changing device, and at least one of heating or cooling the exposed surface of the specimen, which is not thermally insulated while the other surfaces of the specimen are thermally insulated, with the temperature changing device.

25. The method of claim 24 wherein disposing the temperature changing device comprises disposing the temperature changing device directly over the internal cavity.

26. The method of claim 22 further comprising disposing a retention cage of the apparatus so that a bottom surface of the retention cage supports the base, at least one side surface of the retention cage is disposed around a perimeter of the base, and an open top end of the retention cage ends at an imaginary plane formed by the first outer surface of the base.

27. The method of claim 22 further comprising determining a thermal performance of the single-sided, thermal shock tested specimen during or as a result of the heating or cooling.

* * * * *